(12) United States Patent
Ostapoff et al.

(10) Patent No.: US 10,016,535 B2
(45) Date of Patent: *Jul. 10, 2018

(54) MEDICAL DEVICES

(71) Applicant: Covidien LP, Mansfield, MA (US)

(72) Inventors: Roland Ostapoff, West Hartford, CT (US); Timothy Sargeant, Pleasanton, CA (US)

(73) Assignee: Covidien LP, Mansfield, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/166,348

(22) Filed: May 27, 2016

(65) Prior Publication Data
US 2016/0317720 A1 Nov. 3, 2016

Related U.S. Application Data

(63) Continuation of application No. 13/826,368, filed on Mar. 14, 2013, now Pat. No. 9,364,199.

(51) Int. Cl.
| *A61B 17/08* | (2006.01) |
| *A61L 31/16* | (2006.01) |
| *A61L 27/54* | (2006.01) |
| *A61L 27/58* | (2006.01) |
| *A61L 31/14* | (2006.01) |
| *A61L 17/00* | (2006.01) |
| *A61B 17/00* | (2006.01) |
| *A61M 37/00* | (2006.01) |
| *A61L 17/10* | (2006.01) |
| *A61L 31/04* | (2006.01) |

(52) U.S. Cl.
CPC ............... *A61L 31/16* (2013.01); *A61B 17/00* (2013.01); *A61L 17/005* (2013.01); *A61L 17/10* (2013.01); *A61L 27/54* (2013.01); *A61L 27/58* (2013.01); *A61L 31/04* (2013.01); *A61L 31/041* (2013.01); *A61L 31/042* (2013.01); *A61L 31/148* (2013.01); *A61M 37/00* (2013.01); *A61L 2300/604* (2013.01)

(58) Field of Classification Search
CPC ........ A61L 27/54; A61L 27/58; A61L 31/148; A61L 17/005; A61L 31/16; A61L 17/10; A61L 31/04; A61L 31/041; A61L 31/042; A61L 2300/604; A61M 37/00; A61B 17/00

See application file for complete search history.

(56) References Cited

U.S. PATENT DOCUMENTS

| 3,490,675 A | 1/1970 | Green et al. |
| 4,300,565 A | 11/1981 | Rosensaft et al. |
| 4,681,588 A | 7/1987 | Ketharanathan |

(Continued)

FOREIGN PATENT DOCUMENTS

| EP | 2386321 A2 | 11/2011 |
| WO | 2008109123 A2 | 9/2008 |
| WO | 2011067569 A1 | 6/2011 |

OTHER PUBLICATIONS

Extended European Search Report from Application No. EP 14159420.0 dated Jan. 5, 2015.

(Continued)

*Primary Examiner* — Eric Rosen
*Assistant Examiner* — Son Dang

(57) ABSTRACT

The present disclosure provides medical devices possessing reactants thereon, which further promote adherence of the device to tissue in vivo and/or release of bioactive agents from the device.

25 Claims, 4 Drawing Sheets

(56) References Cited

U.S. PATENT DOCUMENTS

| | | |
|---|---|---|
| 5,040,715 A | 8/1991 | Green et al. |
| 5,157,111 A | 10/1992 | Pachence |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,332,142 A | 7/1994 | Robinson et al. |
| 5,468,253 A | 11/1995 | Bezwada et al. |
| 5,707,385 A | 1/1998 | Williams |
| 5,810,855 A | 9/1998 | Rayburn et al. |
| 5,874,500 A | 2/1999 | Rhee et al. |
| 5,915,616 A | 6/1999 | Viola et al. |
| 5,964,394 A | 10/1999 | Robertson |
| 6,083,522 A | 7/2000 | Chu et al. |
| 6,165,201 A | 12/2000 | Sawhney et al. |
| 6,241,139 B1 | 6/2001 | Milliman et al. |
| 6,273,897 B1 | 8/2001 | Dalessandro et al. |
| 6,330,965 B1 | 12/2001 | Milliman et al. |
| 6,495,127 B1 | 12/2002 | Wallace et al. |
| 6,566,406 B1 | 5/2003 | Pathak et al. |
| 6,818,018 B1 | 11/2004 | Sawhney |
| 6,887,974 B2 | 5/2005 | Pathak |
| 7,009,034 B2 | 3/2006 | Pathak et al. |
| 7,129,210 B2 | 10/2006 | Lowinger et al. |
| 7,332,566 B2 | 2/2008 | Pathak et al. |
| 8,288,477 B2 | 10/2012 | Hadba et al. |
| 9,364,199 B2 | 6/2016 | Ostapoff et al. |
| 2003/0120284 A1 | 6/2003 | Palacios et al. |
| 2004/0043017 A1 | 3/2004 | Masci et al. |
| 2004/0175408 A1 | 9/2004 | Chun et al. |
| 2005/0113938 A1 | 5/2005 | Jamiolkowski et al. |
| 2005/0208100 A1 | 9/2005 | Weber et al. |
| 2005/0245965 A1 | 11/2005 | Orban, III et al. |
| 2006/0085034 A1 | 4/2006 | Bettuchi |
| 2006/0115457 A1 | 6/2006 | Hnojewyj |
| 2006/0135992 A1 | 6/2006 | Bettuchi et al. |
| 2006/0173470 A1 | 8/2006 | Oray et al. |
| 2007/0185231 A1 | 8/2007 | Liu et al. |
| 2008/0064839 A1 | 3/2008 | Hadba et al. |
| 2008/0132941 A1 | 6/2008 | Sullivan et al. |
| 2009/0104474 A1 | 4/2009 | Schwartz et al. |
| 2009/0143819 A1 | 6/2009 | D'Agostino |
| 2009/0162337 A1 | 6/2009 | Gross et al. |
| 2010/0312275 A1 | 12/2010 | Euteneuer et al. |
| 2010/0331880 A1 | 12/2010 | Stopek |
| 2011/0008404 A1 | 1/2011 | Lyon et al. |
| 2011/0293669 A1 | 12/2011 | Bennett et al. |
| 2011/0293687 A1 | 12/2011 | Bennett et al. |
| 2011/0293688 A1 | 12/2011 | Bennett et al. |
| 2011/0293692 A1 | 12/2011 | Bennett et al. |
| 2011/0293699 A1 | 12/2011 | Bennett et al. |
| 2012/0049689 A1 | 3/2012 | Bennett et al. |
| 2012/0064299 A1 | 3/2012 | Bennett et al. |
| 2012/0145767 A1 | 6/2012 | Shah et al. |
| 2012/0241493 A1 | 9/2012 | Baxter, III et al. |
| 2012/0273547 A1 | 11/2012 | Hodgkinson et al. |
| 2013/0041406 A1 | 2/2013 | Bear et al. |
| 2013/0112731 A1 | 5/2013 | Hodgkinson |
| 2013/0153635 A1 | 6/2013 | Hodgkinson |

OTHER PUBLICATIONS

R.N. Dave et al., "Novel Biocatalytic Polymer-Based Antimicrobial Coatings as Potential Ureteral Biomaterial: Preparation and In Vitro Performance Evaluation", Antimicrobial Agents and Chemotherapy, vol. 55, No. 2, pp. 845-853 (2010).

EP Examination Report issued in Appl. No. EP 14159420.0-1455 dated Jul. 8, 2016.

MEDICAL DEVICES

CROSS-REFERENCE TO RELATED APPLICATIONS

This application is a continuation of U.S. patent application Ser. No. 13/826,368 filed Mar. 14, 2013, and the disclosures of the above-identified application is hereby incorporated by reference in its entirety.

TECHNICAL FIELD

The present disclosure relates to medical devices, and more particularly to medical devices possessing reactants thereon, which can enhance adherence of the device to tissue and/or release of bioactive agents from the device.

BACKGROUND OF RELATED ART

Medical devices, such as staples and sutures, are commonly used in surgeries, for example, to resect tissues, transect tissues, and to create connections between tissues and organs. These medical devices may possess coatings thereon which, in embodiments, may further include bioactive agents.

Other devices, such as meshes, combination mesh products, or other porous prostheses are commonly used to provide a physical barrier between types of tissue or extra strength to a physical defect in soft tissue. These devices are often affixed to tissue using additional medical devices, such as staples and sutures as described above. These devices may also possess coatings thereon, to provide desirable properties, including handling characteristics, and may also have bioactive agents as part of the coatings.

Improved medical devices, with enhanced ability to release bioactive agents therefrom, remain desirable.

SUMMARY

The present disclosure provides medical devices and methods for forming same. In embodiments, a medical implant of the present disclosure includes a first component including a first reactant in combination with at least one bioactive agent; and a second component including a second reactant, wherein the second reactant degrades the first reactant, thereby releasing the bioactive agent in vivo.

The first component may be, in embodiments, tapes, felts, scaffolds, patches, pledgets, mesh, and/or buttresses. The second component may be, in embodiments, staples, sutures, clips, tacks, screws, pins, anchors, fasteners, sheaths, shunts, tissue barriers, stents and/or grafts.

In embodiments, the first reactant includes hydrolytically degradable bonds and the second reactant comprises an acid or weak base which adjusts the pH adjacent the implant, enhancing hydrolysis of the degradable bonds. In other embodiments, the first reactant includes an enzymatically degradable linkage, and the second reactant includes an enzyme.

In other embodiments, medical implant of the present disclosure may include a buttress possessing a first reactant and at least one bioactive agent; and at least one staple including a second reactant, wherein the second reactant degrades the first reactant, thereby releasing the bioactive agent in vivo.

BRIEF DESCRIPTION OF FIGURES

Various embodiments of the present disclosure are described hereinbelow with reference to the drawings, wherein.

DETAILED DESCRIPTION

Figure 1:
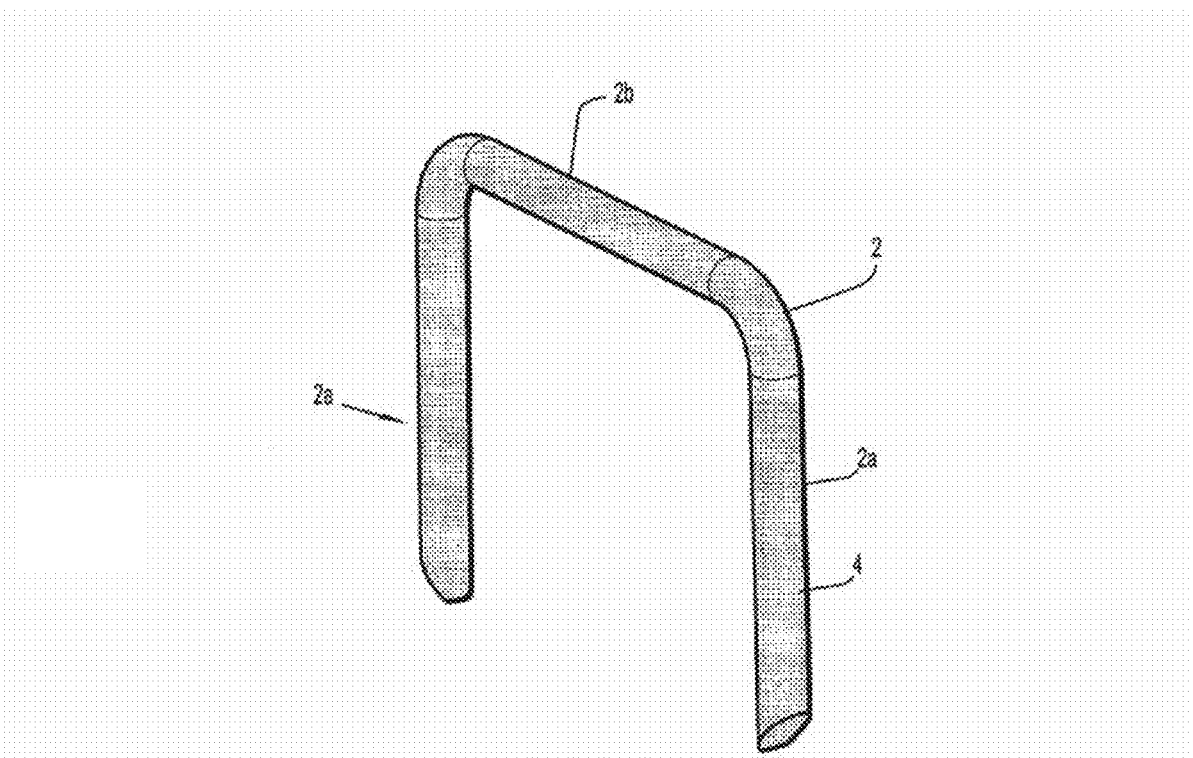
FIG. 1 is a side perspective view of a surgical staple including a staple coating possessing a first reactant in accordance with the present disclosure.

The present disclosure is directed to medical devices that possess reactants thereon. In embodiments, the medical devices may be multi-component wound closure devices, where at least a first component of the wound closure device possesses a first reactant and a second component of the wound closure device possesses a second reactant. The first and second reactants are disposed on or within the components of the medical device in an unreacted state. The first reactant reacts in situ with the second reactant upon implantation or application of the medical device to tissue.

In embodiments, the first reactant is a degradable linkage, and the second reactant is an enzyme or similar component capable of reacting with, or otherwise promoting the cleaving of, a bond that is part of the first reactant. Thus, where the first reactant possesses or binds a bioactive agent to the first component of the medical device, contact with the second component of the medical device possessing the second reactant may result in hydrolysis and/or enzymatic cleavage of the first reactant, thereby releasing the bioactive agent from the first component.

As used herein, the term "tissue" includes, but is not limited to, tissues such as lung, bowel, skin, fat, fascia, bones, muscles, tendons, ligaments, solid organs, lumens, ducts, lymphatics, nerves, and blood vessels.

As used herein, the term "physiologic fluid" includes, but is not limited to fluids such as blood, plasma, peritoneal fluid, cerebral spinal fluid, urine, lymph fluid, synovial fluid, vitreous fluid, saliva, gastrointestinal luminal contents, bile, and gas (e.g., $CO_2$).

In the description that follows, the term "biodegradable" as used herein is defined to include both bioabsorbable and bioresorbable materials. By biodegradable, it is meant that the materials decompose or lose structural integrity within a clinically relevant time period, under body conditions (e.g., enzymatic degradation or hydrolysis), or are broken down (physically or chemically) under physiologic conditions in the body such that the degradation products are excretable or absorbable by the body. In embodiments, biodegradable compositions of the present disclosure may degrade over a period of time from about 1 week to about 12 months, in embodiments from about 2 weeks to about 9 months, in embodiments from about 3 weeks to about 7 months, in embodiments from about 1 month to about 6 months.

In general, medical devices of the present disclosure possess a first component including a first reactant and a second component including a second reactant. As noted above, in embodiments, the first reactant, second reactant, or both, may include degradable linkages.

For example, in embodiments, the first reactant may include hydrolytically degradable bonds, so that the first component becomes biodegradable. Hydrolytically degradable bonds can be incorporated into the first component, for example a polymeric first component, by forming the polymer using monomers that include, but are not limited to, hydrolytically labile α-hydroxy acids such as lactic acid, glycolic acid, lactide and glycolide, lactones including ε-caprolactone, carbonates such as trimethylene carbonate, ester ethers such as dioxanones, diacids including azelaic acid, succinnic acid, adipic acid, sebacic acid, malonic acid, glutaric acid, and the like, phosphoesters such as ethyl dichlorophosphate, anhydrides including azelaic acid anhydride and sebacic acid anhydride, combinations thereof, and the like.

Other suitable monomers for use in forming the first reactant include, for example, polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxymethylcellulose, hyaluronic acid, and proteins such as albumin, collagen, casein, gelatin, combinations thereof, and the like.

Those skilled in the art will readily envision reaction schemes for incorporating hydrolytically degradable linkages into the first reactant. As noted above, degradable monomers may be used in forming the first reactant. Alternatively, or in addition, functional groups of precursors used to form the first reactant may be chosen such that the product of the reaction between them results in a degradable linkage.

Where the first reactant possesses hydrolytically degradable bonds, the second reactant may be capable of releasing water in situ and/or otherwise degrading the hydrolytically degradable bonds. For example, acidic agents may be used as the second reactant, which are capable of adjusting the pH of bodily fluid at or adjacent the medical device. The presence of the acid adjusts the pH of bodily fluid adjacent the medical device to a pH from about 5 to about 7.5, in embodiments from about 6.5 to about 7.2. This pH may increase and/or enhance the degradation of the first reactant. Suitable acids include, for example, mild organic acids such as lactic acid, citric acid, acetic acid, stearic acid, salicylic acid, combinations thereof, and the like.

In other embodiments, polymers having acid functional groups thereon, for example carboxylic acids, sulfonic acids, combinations thereof, and the like, may be used as the second reactant. Polymers possessing such functional groups are commercially available and/or may be readily synthesized utilizing means within the purview of one skilled in the art.

In yet other embodiments, where the first reactant possesses hydrolytically degradable bonds, basic agents may be used as the second reactant, which are capable of adjusting the pH of bodily fluid at or adjacent the medical device. The presence of the base may adjust the pH of bodily fluid adjacent the medical device to a pH from about 7.5 to about 9.5, in embodiments from about 7.7 to about 8.5. This pH may increase and/or enhance the degradation of the first reactant. Suitable bases include weak bases such as carbonates, buffer salts including phosphates, proteins, combinations thereof, and the like.

In addition to, or in place of, components that provide hydrolytically degradable linkages, at least one linkage that is enzymatically degradable may be incorporated into the first reactant so that it becomes biodegradable.

Examples of enzymatically degradable linkages include peptidic linkages. Cleavage of a portion of a first reactant by enzymes means that an enzyme has a preference for a particular chemical group in a first reactant as compared to most other chemical groups. In addition, proteins may generally be considered to be enzymatically cleavable since most proteins have specific sequences that are susceptible to enzymatic degradation.

Other exemplary linkages which are enzymatically degradable include, but are not limited to: an amino acid residue such as -Arg-, -Ala-, -Ala(D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Gln-Ala-Arg-, -Gln-Gly-Arg-, -Asp-Pro-Arg-, -Gln(Arg)$_2$-, Phe-Arg-, -(Ala)$_3$-, -(Ala)$_2$-, -Ala-Ala(D)-, -(Ala)$_2$-Pro-Val-, -(Val)$_2$-, -(Ala)$_2$-Leu-, -Gly-Leu-, -Phe-Leu-, -Val-Leu-Lys-, -Gly-Pro-Leu-Gly-Pro-, -(Ala)$_2$-Phe-, -(Ala)$_2$-Tyr-, -(Ala)$_2$-His-, -(Ala)$_2$-Pro-Phe-, -Ala-Gly-Phe-, -Asp-Glu-, -(Glu)$_2$ -Ala-Glu-, -Ile-Glu-, -Gly-Phe-Leu-Gly-, -(Arg)$_2$-; D-glucose, N-acetylgalactosamine, N-acetylneuraminic acid, N-acetylglucosamine, N-acetylmannnosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine, and the like. Combinations of the foregoing enzymatically degradable linkages may be used in embodiments. Those skilled in the art will readily envision reaction schemes for incorporating enzymatically degradable linkages into the first reactant.

Where the first reactant is an enzymatically degradable linkage, the second first reactant may be an enzyme capable of degrading that linkage. For example, peptidic linkages are cleavable by proteases, metalloproteinases, collagenases, combinations thereof, and the like.

In embodiments, the first and second components of a medical implant of the present disclosure may include hydrogel precursors. For example, the first component or second component may include natural or synthetic multifunctional primary amines. The term "multifunctional" as used herein means the primary amine includes at least two primary amine groups. Suitable natural or derived primary amines are found in materials (including tissues) such as collagen, albumin, elastin, polysaccharides such as chitosan, aminated dextran, modified cellulose and hyaluronic acid, polylysine or peptides and/or proteins with lysine residues (including pegylated or macromers versions), polyarginine or peptides and/or proteins with arginine residues (including pegylated or macromers versions), polyhistidine or peptides and/or proteins with histidine residues (including pegylated or macromers versions) and combinations thereof. Suitable synthetic amines include vinyl monomers with primary amine functionality (e.g., acrylamide) and copolymers thereof, lysine modified polyesters (PLA), polyethylene glycol (PEG), PEG polypropylene glycol, PEG-co-silicone and combinations thereof. Other suitable multifunctional amines include those listed above.

Additional materials suitable for use in forming a first component or a second component of a medical implant of the present disclosure include materials such as succinimidyl functional polymers such as N-hydroxysuccinimide esters (NHS), N-hydroxysulfosuccinimide esters (SNHS), N-hydroxyethoxylated succinimide esters (ENHS) and combinations thereof. Succinimidyl-based esters are reactive with the above-mentioned multifunctional primary amines.

In general, it should be understood that where a first component includes a NHS ester reactive group, the second component includes a multifunctional primary amine presenting surface. In such an embodiment, in addition to having a first component possessing a first reactant that is degraded by the second reactant on the second component, the first component and second component may also react to form a hydrogel as part of a medical implant of the present disclosure.

In additional embodiments, the first or second component may include electrophilic functional groups while the second component includes nucleophilic functional groups, or vice-versa. Electrophilic functional groups include the succinimidyl containing polymers described above, such as SNHS and ENHS. Additional non-limiting examples of electrophilic groups include carbonylimidazoles, isocyanates, vinylsulfones, maleimides, and p-nitrophenyls. Suitable nucleophilic functional groups include natural and synthetic multifunctional primary amines such as those listed above, in addition to thiol groups. Other suitable first and second nucleophilic and electrophilic components and methods of making are disclosed in U.S. Pat. Nos. 6,887,974; 7,332,566; 6,566,406; 7,009,034; 6,165,201; 6,818,018; and U.S. Patent Application Publication No. 2010/0331880, the entire disclosures of each of which are incorporated by reference herein.

Where the first and second components react to form hydrogels, the components may possess biocompatible and water soluble core groups. As used herein, water soluble refers to a solubility of at least about 1 g/l in water. This core group may be a water soluble molecule with a minimum of three arms. An arm of a core group refers to a linear chain of chemical groups that connect a crosslinkable functional group as well as a first or second reactant to a multifunctional center which initiates the polymerization of the polymeric arms. The combination of this multifunctional center and the attached arms may form the core group.

In embodiments, the core group may be a water soluble polymer. Examples of such polymers that may be used include, for example: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers; vinyl polymers such as polyvinyl alcohol ("PVA") and poly (vinyl pyrrolidinone) ("PVP"); proteins such as poly (amino acids); polysaccharides such as dextran, as well as derivatives of the foregoing and combinations of the foregoing.

In other embodiments, multifunctional centers may include polyols which, in embodiments, may possess hydroxyl groups for initiation of monomeric groups that may form the arms of the core that can then be functionalized with crosslinkable groups, as well as first and/or second reactants. Depending on the desired number of arms, the polyol may possess from about 3 to about 12 hydroxyl groups, in embodiments from about 4 to about 10 hydroxyl groups. The polyol may also possess first and/or second reactants. Suitable polyols include glycerol, mannitol, reducing sugars such as sorbitol, pentaerythritol, and glycerol oligomers including hexaglycerol, as well as derivatives thereof and combinations thereof. As would be readily apparent to one skilled in the art, the number of hydroxyl groups should be equivalent to the number of arms on the multi-armed core, i.e., the particular polyol chosen should determine the number of arms on the resultant multifunctional core group. In some embodiments, the arms may include degradable linkages, as described above, incorporated therein.

In embodiments, a polymer described above, such as polyethylene glycol, may be formed by initiating the polymerization of ethylene oxide with the polyol, thereby forming arms of a multi-armed core that may be further functionalized with components capable of reacting to form a hydrogel, as well as the first and second reactants described above.

Thus, hydrogels can be made from a multi-armed core with a first set of functional groups capable of forming a hydrogel and a first reactant, combined with a low molecular weight polymer having a second set of functional groups capable of forming a hydrogel and a second reactant. The number of arms on the multi-armed core may be from about 3 to about 12, in embodiments from about 5 to about 10. In addition to the first set of functional groups, a first precursor may also possess degradable linkages as described above as a first reactant, while the second precursor may possess both functional groups capable of reacting with the first functional groups to form a hydrogel, as well as a second reactant capable of degrading the degradable linkages.

In embodiments, the first reactant may tether or link a bioactive agent to the first component of the medical device. As used herein, a "tether", "link" or "linker", are synonymous, and refer to any polymer, any portion thereof, or any other material used to immobilize one or more bioactive agents on the first component of a medical device of the present disclosure. In embodiments, the first reactant may be a polymer possessing functional groups capable of linking one or more bioactive agents to the first component of the medical device of the present disclosure. The tether can be either linear or branched with one or more sites for immobilizing bioactive agents. The tether can be any suitable length.

In other embodiments, a bioactive agent may be incorporated in a polymeric matrix coating formed of a first reactant on the first component, with the second reactant degrading the coating, thereby releasing the bioactive agent from the coating.

In use, the second reactant, upon contact with the first reactant, hydrolyzes and/or enzymatically cleaves the first reactant, thereby releasing any bioactive agent linked to the first component of the medical device by the first reactant.

Exemplary reaction pairs of first reactant and second reactant include:

Collagen or peptide-based hydrogels or tethers with collagenase or other enzymes;
RNA with RNase (as hydrogel or tethering chain);
DNA with DNase (as hydrogel or tethering chain); and/or
Calcium cross-linked alginate with calcium-chelators.

Bioactive agents include pharmaceutical and medicinal agents. Medicinal agents which may be introduced as part of the implant include antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes antibiotics, quorum sensing blockers, surfactants, metal ions, antimicrobial proteins and peptides, antimicrobial polysaccharides, antiseptics, disinfectants, anti-virals, anti-fungals, quorum sensing blockers, and combinations thereof. Examples of suitable antiseptics and disinfectants which may be combined with the present disclosure include hexachlorophene, cationic biguanides like chlorhexidine and cyclohexidine, iodine and iodophores like povidone-iodine, halo-substituted phenolic compounds like PCMX (e.g., p-chloro-m-xylenon, furan medical preparations like nitrofurantoin and nitrofurazone, methanamine, aldehydes like gluteraldehyde and formaldehyde, alcohols, combinations thereof, and the like. In some embodiments, at least one of the antimicrobial agents may be an antiseptic, such as triclosan.

Classes of antibiotics that can be combined with the present disclosure include tetracyclines like minocycline, rifamycins like rifampin, macrolides like erythromycin, penicillins like nafcillin, cephalosporins like cefazolon, beta-lactam antibiotics like imipenem and aztreonam, aminoglycosides like gentamicin and TOBRAMYCIN®, chloramphenicol, sulfonamides like sulfamethoxazole, glycopeptides like vancomycin, quinolones like ciprofloxacin, fusidic acid, trimethoprim, metronidazole, clindamycin, mupirocin, polyenes like amphotericin B, azoles like fluconazole, and beta-lactam inhibitors like sulbactam. Other antimicrobials which may be added include, for example, antimicrobial peptides and/or proteins, antimicrobial polysaccharides, quorum sensing blockers (e.g., brominated furanones), anti-virals, metal ions such as ionic silver and ionic silver glass, surfactants, chemotherapeutic drug, telomerase inhibitors, other cyclic monomers including 5-cyclic monomers, mitoxantrone, and the like.

In some embodiments, suitable bioactive agents which may be used include colorants, dyes, preservatives, protein and peptide preparations, antibodies and nanobodies, protein therapeutics, polysaccharides such as hyaluronic acid, lectins, lipids, probiotics, angiogenic agents, anti-thrombotics, anti-clotting agents, clotting agents, analgesics, anesthetics, wound repair agents, chemotherapeutics, biologics, anti-inflammatory agents, anti-proliferatives, diagnostic agents, antipyretic, antiphlogistic and analgesic agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents, dysuric agents, brominated or halogenated furanones, and the like and combinations thereof.

In some embodiments, polymer drugs (polymeric forms of such compounds for example, polymeric antibiotics, polymeric antiseptics, polymeric chemotherapeutics, polymeric anti-proliferatives, polymeric antiseptics, polymeric non-steroidal anti-inflammatory drugs (NSAIDS) and the like) may be utilized and combinations thereof.

In certain embodiments, implants of the present disclosure may contain suitable medicinal agents such as viruses and cells, peptides, polypeptides and proteins, analogs, muteins, and active fragments thereof, such as immunoglobulins, antibodies (monoclonal and polyclonal), cytokines (e.g., lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.) hormones and hormone analogs (e.g., growth hormone), vaccines (e.g., tumoral, bacterial and viral antigens), somatostatin, antigens, blood coagulation factors, growth factors, protein inhibitors, protein antagonists, and protein agonists, nucleic acids, such as antisense molecules, DNA, RNA, oligonucleotides, polynucleotides and ribozymes, viral particles, and combinations thereof. It should be understood that the degradation mechanisms of implants according to the present disclosure may be tailored to provide specific release rates, wherein the degradation of certain materials may correspond to an elution or release of a bioactive agent.

Methods for combining the above mentioned bioactive agents with materials of the present disclosure are within the purview of those skilled in the art and include, but are not limited to, mixing, blending, compounding, spraying, wicking, solvent evaporating, dipping, brushing, vapor deposition, coextrusion, capillary wicking, film casting, molding and the like. Additionally, solvents may be used to incorporate various agents into the implant. Suitable solvents include, but are not limited to, polar and non-polar solvents such as alcohols, e.g., methanol, ethanol, propanol, chlorinated hydrocarbons (e.g., methylene chloride, chloroform, 1,2-dichloro-ethane), and aliphatic hydrocarbons such as hexane, heptene, and ethyl acetate.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

Bioactive agents incorporated into implants of the present disclosure may have various release profiles include, but not limited to, zero order, first order, second order release profiles and combinations thereof. It is also within the purview of one skilled in the art to modify materials to be more hydrophobic or hydrophilic to achieve desired bioactive agent release results. As previously mentioned, bioactive agents and materials may both be altered to achieve specific release mechanisms to correspond with the integration of the implant into tissue.

As noted above, medical devices of the present disclosure may, in embodiments, include two components. For example, in some embodiments, a medical device may include at least one reinforcing material as a first component, and a wound closure device as a second component. Exemplary reinforcing materials include, but are not limited to, reinforcing devices such as pledgets, buttresses, patches, scaffolds, tapes, anchors including bone anchors, meshes (including biologic and composite mesh), and the like. Suitable wound closure devices include, but are not limited to, staples, sutures, clips, tacks, screws, pins, fasteners, sheaths, shunts, tissue barriers, stents, grafts, and the like.

Figure 2:
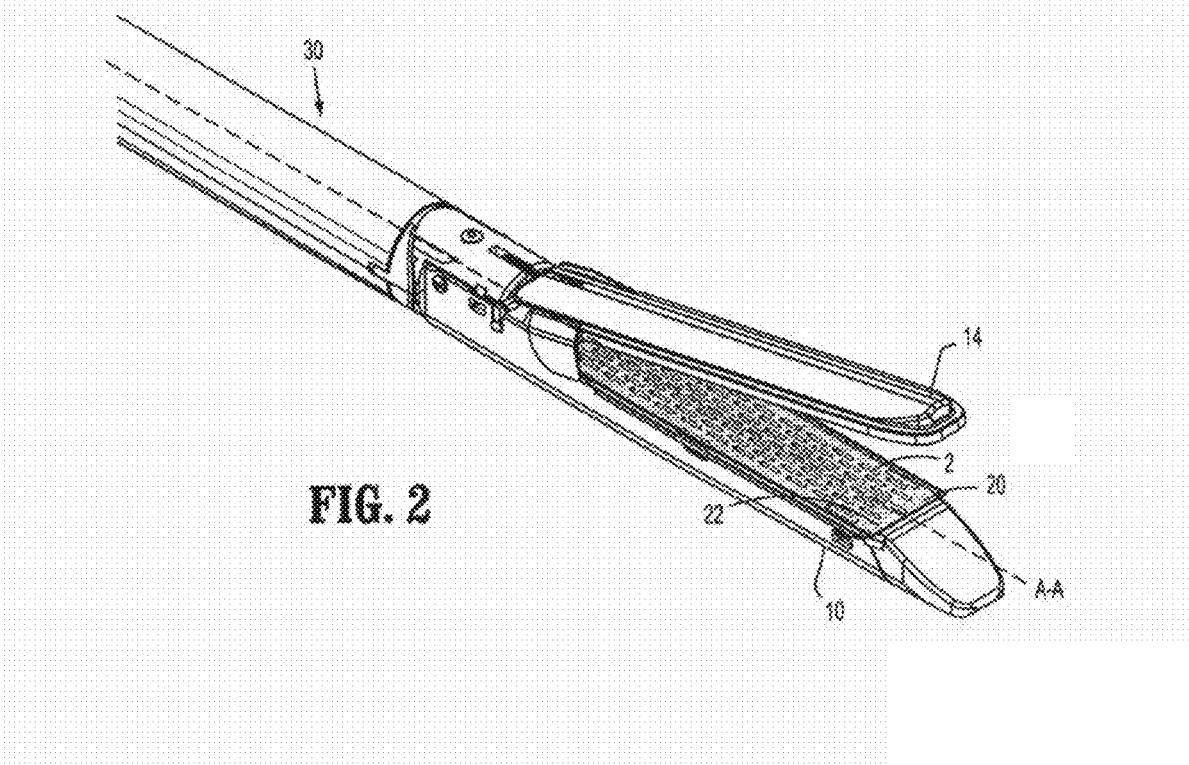
FIG. 2 is a side perspective view of a surgical stapler including a reinforcing material possessing a second reactant in accordance with the present disclosure.
Figure 3:
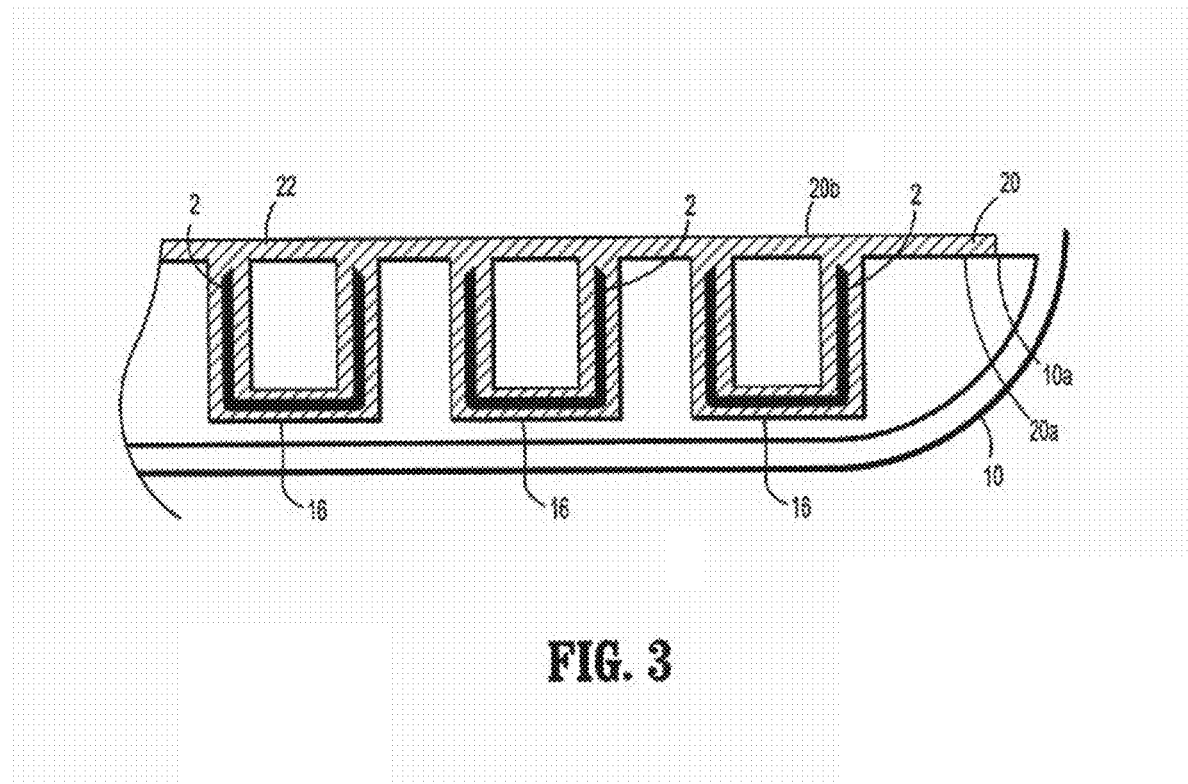
FIG. 3 is a cross-sectional view of a surgical staple cartridge along line A-A of FIG. 2, including staples.

FIGS. 1-3 illustrate an embodiment of the present disclosure including a staple 2 (wound closure device) coated with a second reactant which is paired in situ with a buttress 20 (reinforcing material) including the first reactant. More specifically, FIG. 1 illustrates the staple 2 which is coated with a second reactant 4. In general, staple 2 includes staple legs 2a, connected therebetween by a staple backspan 2b. The second reactant 4 is illustrated in the form of a coating, although the second reactant may be present on the staple in other forms, including but not limited to compounding the reactant within a polymer resin, selective application of localized depots of a reactant, or otherwise embedding an unreacted, second reactant within the medical device. Staples 2 may be coated, for example, using a dip coating technique, although other coating methods are within the purview of those skilled in the art and will be discussed later.

As illustrated, the entire staple 2 is coated, however it is also envisioned that only a portion of the staple 2 may be coated. For example, in certain embodiments, the staple legs 2a may be coated while the staple backspan 2b remains uncoated.

In alternate embodiments, the staple may have a patterned coating disposed thereon for selective surfaces of the staple to crosslink with first reactant (and/or tissue). It is also envisioned that different rows of staples (in a surgical stapler, such as an ENDOGIA™ from Covidien, North Haven, Conn.) may have different reactants or may include different patterns of reactants on the staple surface.

Moving to FIGS. 2-3, a plurality of staples 2 are positioned in a loading unit 30 for firing the staples 2 into tissue. FIG. 2, illustrates a buttress 20 includes a first reactant. The buttress 20 is illustrated, for example, as a single polymer laminar sheet, it being understood that the buttress is not limited to a single laminar sheet. The first reactant 22 is illustrated in the form of a coating, although the first reactant 22 may be present on the buttress 20 in other forms such as compounding within the resin, selective weaving of threads/filaments within the buttress, or selective application of localized depots of a reactant. Buttress 20 may be coated using any technique within the purview of those skilled in the art. As illustrated, the entire buttress 20 is coated, however it is also envisioned that only a portion of the buttress 20 may be coated. For example, in certain embodiments, a first surface 20a of the buttress may include a reactant, while a second surface 20b does not include the reactant.

In alternate embodiments, the first and second surfaces of the buttress may be coated or otherwise contain different reactants. For example, a first surface 20a may be coated with a first reactant (to react with the second reactant), while the second surface 20b may be coated with a third reactant to selectively crosslink to the tissue surface. The reinforcing material may also have the first reactant selectively patterned on the surface or selectively incorporated/positioned within the reinforcing material (e.g., localized depots).

The buttress 20 is positioned adjacent the staple cartridge 10 (FIGS. 2-3) however, it is also contemplated that the buttress 20 be positioned with respect to the anvil 14, or the buttress 20 may be positioned with respect to both the cartridge 10 and the anvil 14. It is also envisioned that the buttress 20 may be provided pre-loaded on the loading unit 30 or, in the alternative, the buttress 20 may be attached to the loading unit 30 in the operating room prior to implantation. One example of an integrated buttress which may be employed is DUET TRS™ (Covidien, North Haven, Conn.), disclosed in U.S. Provisional Patent Application No. 60/905,532, filed Mar. 6, 2007, the entire disclosure of which is incorporated by reference herein.

Figure 4A:
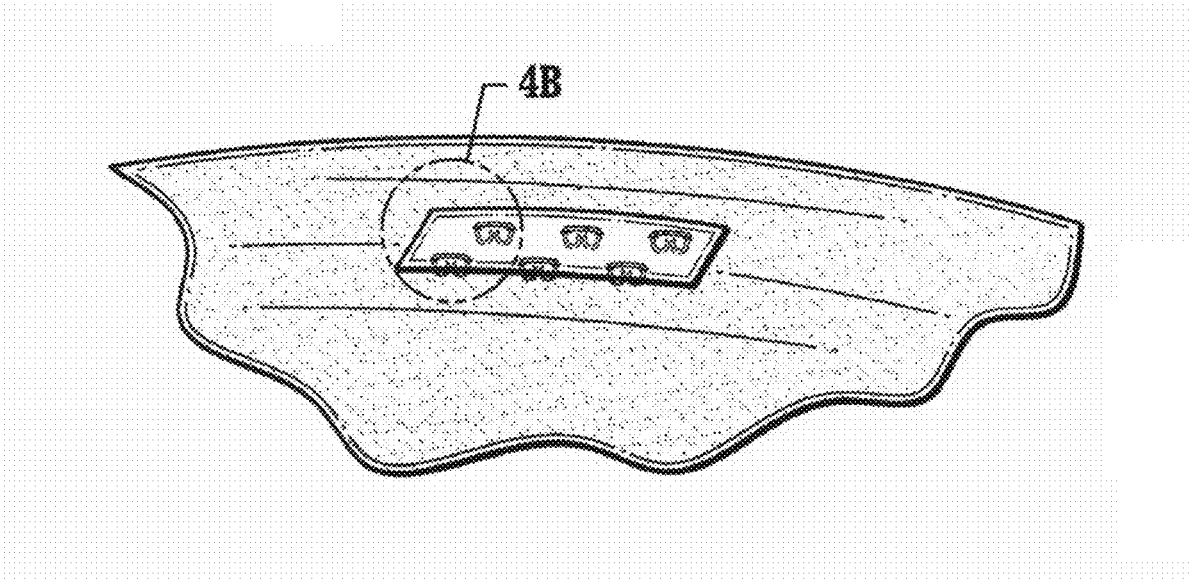
FIG. 4A is a perspective view of one embodiment of the present disclosure, illustrating staples fired through a buttress into tissue.
Figure 4B:
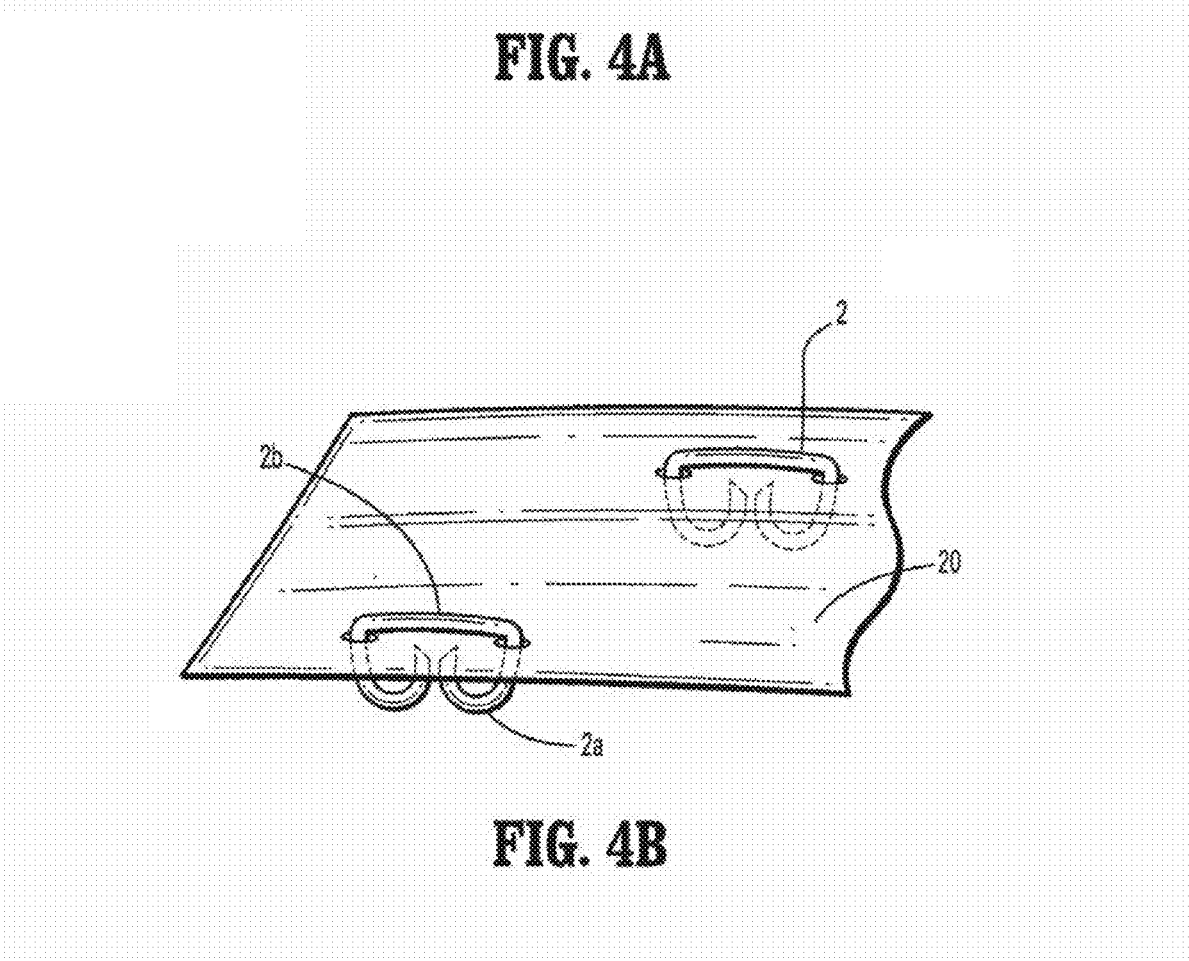
FIG. 4B is an enlarged view of a portion of FIG. 4A.

FIG. 3 illustrates another view of a row of staples 2 in the staple pockets 16 taken along line "A-A". The buttress 20 is placed adjacent the cartridge surface 10a such that when the staples 2 are fired, the staples' legs 2a first penetrate the buttress 20, then pierce a first tissue surface (not shown), the staple legs 2a next exit a second tissue surface (not shown), where the staple legs 2a contact the staple buckets (not shown) on the anvil 14, bending the staple legs 2a back into the second tissue surface, completing a substantially "B" shaped staple formation as illustrated in FIGS. 4A-4B. As the staples 2 are fired through the buttress 20 in situ, a medical device is produced. Physiologic fluids mix the first and second reactants together, initiating a chemical reaction, and release of bioactive agents.

Figure 5:
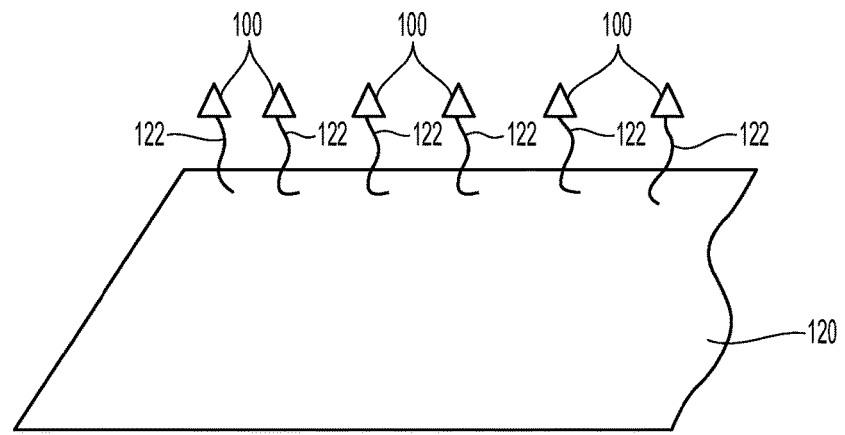
FIG. 5 is a perspective view of a component of a medical implant of the present disclosure possessing a bioactive agent linked thereto by a reactant.

Turning to FIG. 5, FIG. 5 depicts a bioactive agent 100 tethered to a first component 120 of a medical device by a first reactant 122. In use, upon contacting the second component possessing the second reactant (not shown) with the first component, the second reactant cleaves the first reactant 122, thereby releasing bioactive agent 100 from first component 120. So, for example, where the first component 120 is a buttress or similar material, a tack or staple possessing a second reactant capable of degrading or cleaving first reactant 122 may be used to both affix the first component to tissue and release the bioactive agent therefrom.

Figure 6:
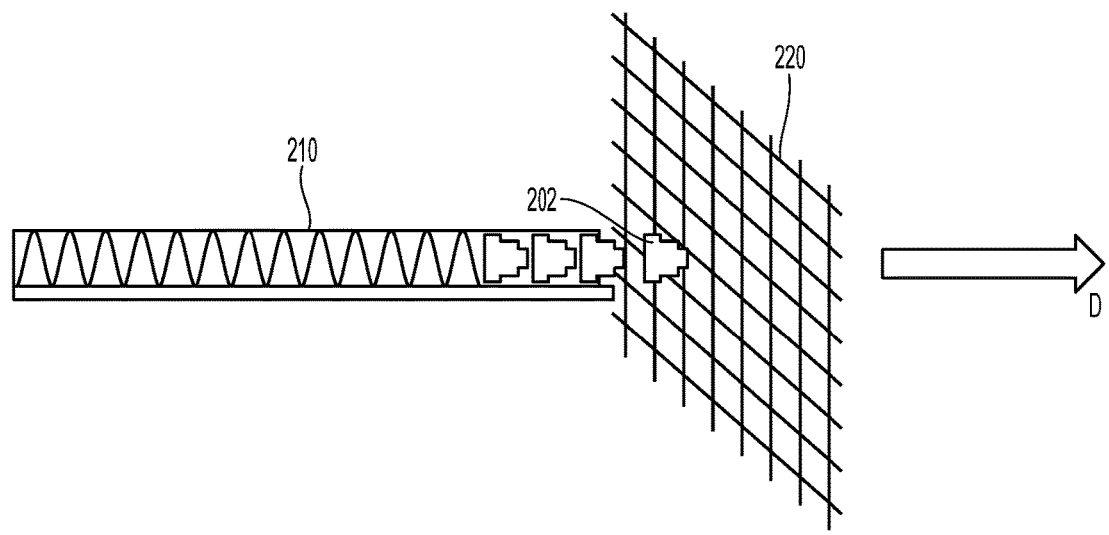
FIG. 6 depicts affixing a medical implant of the present disclosure to tissue, demonstrating a mesh having a first reactant thereon, affixed to tissue by a tack having a second reactant thereon.

In other embodiments, as noted above, a tack and mesh may be used in combination to form an implant of the present disclosure. Such a usage is depicted in FIG. 6. As shown in FIG. 6, tacks 202 may be dispensed from a suitable dispenser 210 through mesh 220 in direction "D" into tissue. As noted above, but not depicted in FIG. 6, the tack possesses one of the reactants, with the mesh possessing the other reactant. In other words, the tack may have a second reactant thereon, and the mesh may have a first reactant thereon, or vice-versa. A bioactive agent (not shown) may be on tacks 202, mesh 220, or both, and may be released upon contact of the first reactant with the second reactant.

In some embodiments, the mesh may be formed of a fiber having a core/sheath construction. Examples of such fibers and meshes formed therefrom include those disclosed in U.S. Patent Application Publication Nos. 2010/0189764 and 2011/0190795, the entire disclosures of each of which are incorporated by reference herein. The core of the fiber may include one reactant, with the tack including the second reactant. In use, the act of securing the mesh to tissue with the tack will damage the filament, allowing the reactant in the core to react with the reactant on the tack, thereby releasing the bioactive agent from whichever component possessed the bioactive agent.

In other embodiments, silver may be embedded in the fibers, with an oxidizing agent on the tack. The disruption of the fiber by the tack, possessing the oxidizing agent thereon, may result in a release of a burst of silver ions to enhance the antimicrobial activity of the mesh. After the initial burst, the release of silver ions will be at a maintenance level as the fibers degrade in vivo.

Other exemplary devices include, for example, a bone anchor that has BMP-7 tethered to its surface via an enzyme-cleavable peptide, used in conjunction with a suture that is coated with the enzyme. Once placed in situ, the enzyme releases from the suture and cleaves the peptide, thereby releasing the BMP-7 locally around the bone anchor, speeding up the integration of bone into the porous anchor.

In other embodiments, a mesh may be provided having a calcium-gelled alginate hydrogel coating with bupivacaine. This is used in conjunction with tacks that are coated with a calcium chelator, which binds to the nearby calcium, breaking up the alginate hydrogel, and locally releasing the bupivacaine. In yet other embodiments, the mesh may have a hydrogel coating that is collagen based, and contains growth factors. The tack is coated with collagenase, which breaks down the hydrogel to release the growth factors.

In yet other embodiments, a buttress may be loaded with an RNA-based hydrogel that contains a chemotherapeutic, and affixed to tissue with staples that are coated with RNase. Once applied, the staples trigger release of the chemotherapeutic from the buttress.

In addition to reactants, other materials used to construct medical devices of the present disclosure may include biodegradable materials such as synthetic and natural materials. For example, the reinforcing material illustrated in FIG. 1 may include a glycolide, TMC, dioxanone copolymer which is further coated with a reactant, it being understood that the reinforcing material is not limited to a specific polymer or copolymer. Suitable synthetic biodegradable materials include polymers such as those made from lactide, glycolide, caprolactone, valerolactone, carbonates (e.g., trimethylene carbonate, tetramethylene carbonate, and the like), dioxanones (e.g., 1,4-dioxanone), Δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly (ortho esters), hydroxy alkanoates, tyrosine carbonates, polyimide carbonates, polyimino carbonates such as poly (bisphenol A-iminocarbonate) and poly (hydroquinone-iminocarbonate), polyurethanes, polyanhydrides, polymer drugs (e.g., polydiflunisol, polyaspirin, and protein therapeutics) and copolymers and combinations thereof.

Natural polymers may also be used to construct medical devices of the present disclosure, including but not limited to, collagen, poly (amino acids), polysaccharides such as cellulose (including carboxymethyl cellulose), dextran, chitin, chitosan, alginate and glycosaminoglycans, hyaluronic acid, gut, copolymers and combinations thereof. Collagen as used herein includes natural collagen such as animal derived collagen, or synthetic collagen such as recombinant collagen. Proteins such as elastin, albumin, casein, may also be used in accordance with the present disclosure. Additionally, natural materials include chemical modifications of the above-listed materials such as recombinant, aminated, sulfonated, and carboxylated polymer analogs.

In certain applications, it may be preferred to have at least one of the components of the medical device made of non-biodegradable materials. In one non-limiting example, it may be preferable to have a non-biodegradable wound closure device. Suitable materials include fluorinated polymers (e.g., fluoroethylenes, propylenes, fluoroPEGs), polyolefins such as polyethylene, polyesters such as poly ethylene terepththalate (PET), nylons, polyamides, polyurethanes, silicones, ultra high molecular weight polyethylene (UHMWPE), polybutesters, polyethylene glycol, polyaryletherketone, copolymers and combinations thereof. Additionally, non-biodegradable polymers and monomers may be combined with each other and may also be combined with various biodegradable polymers and monomers to create the medical device.

In certain embodiments, medical devices according to the present disclosure may be constructed at least in part using shape memory polymers. Shape memory polymers are smart materials which have to ability to return from a deformed state (temporary shape) to their original (permanent) shape induced by an external stimulus such as temperature, current, light, pH, etc. Suitable polymers used to prepare hard and soft segments of shape memory polymers include polycaprolactone, dioxanone, lactide, glycolide, polyacrylates, polyamides, polysiloxanes, polyurethanes, polyether amides, polyurethane/ureas, polyether esters, and urethane/butadiene copolymers and combinations thereof.

In other embodiments, metals or metal alloys may be used to form medical devices of the present disclosure. Suitable metals and metal alloys include titanium, nickel titanium, steel, magnesium-based alloys, manganese based-alloys and combinations thereof. Metals or metal alloys of the present disclosure may additionally have shape memory characteristics, or in the alternative, may be biodegradable.

The first and second reactants may be applied to implants or incorporated therein using a variety of methods. In one embodiment, as noted above, the components used to form the medical device, such as wound closure materials and/or reinforcing materials, may include reactants in the form of a coating. Methods for coating medical implants are within the purview of those skilled in the art and include but are not limited to spraying (i.e., ultrasonic or electrospraying), brushing, dipping, drip coating, solvent evaporation, laser and inkjet printing, and the like. The coating compositions may be in the form of a solution, dispersion, emulsion or any other homogeneous or heterogeneous mixture. Additionally, solvents may be used to apply coatings to the implants. Suitable solvents are within the purview of those skilled in the art which include both polar and non-polar solvents.

The first and second reactants may also be incorporated into the device utilizing other methods, for example, the reactant may be embedded or compounded within any resin used to form the medical device. For example, a multifunctional primary amine may be compounded within polyester and extruded (or coextruded) to create an implant such as a fiber. Additionally, such fibers may be braided or interwoven with other fibers to create a multifilament implant such as a braided suture or a mesh. The plurality of filaments may be combined using any technique within the purview of one skilled in the art such as commingling, twisting, braiding, weaving, entangling, and knitting. For example, a plurality of filaments may simply be combined to form a yarn. As another example, a plurality of filaments may be braided.

As previously discussed, medical implants of the present disclosure may, in embodiments, include at least one reinforcing material and one wound closure device. Exemplary reinforcing materials include, but are not limited to, reinforcing devices such as pledgets, buttresses, patches, scaffolds, tapes, felts, and mesh (including biologic and composite mesh). Suitable wound closure devices of the present disclosure include but are not limited to staples, sutures, clips, tacks, screws, pins, anchors, fasteners, sheaths, shunts, tissue barriers, stents and grafts. Medical implants of the present disclosure may include both biodegradable and non-biodegradable materials including those listed above.

Once the implant is constructed, it can be sterilized by any means within the purview of those skilled in the art including but not limited to ethylene oxide, electron beam (e-beam), gamma irradiation, autoclaving, plasma sterilization and the like.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A medical implant comprising:
   a mesh comprising a first reactant and at least one bioactive agent; and
   a fastener for securing the mesh to tissue, the fastener comprising a second reactant,
   wherein the second reactant degrades the first reactant, thereby releasing the bioactive agent in vivo.

2. The medical implant according to claim 1, wherein the fastener is selected from the group consisting of staples, sutures, clips, tacks, screws, pins and anchors.

3. The medical implant according to claim 1, wherein the first reactant comprises hydrolytically degradable bonds and the second reactant comprises an acid.

4. The medical implant according to claim 3, wherein the acid adjusts the pH of bodily fluid adjacent the medical implant to a pH from about 5 to about 7.5.

5. The medical implant according to claim 3, wherein the first reactant comprises a polymer possessing monomers selected from the group consisting of lactic acid, glycolic acid, lactide, glycolide, ε-caprolactone, trimethylene carbonate, dioxanones, azelaic acid, succinnic acid, adipic acid, sebacic acid, malonic acid, glutaric acid, ethyl dichlorophosphate, azelaic acid anhydride, sebacic acid anhydride, and combinations thereof.

6. The medical implant according to claim 3, wherein the second reactant is an acid selected from the group consisting of lactic acid, citric acid, acetic acid, stearic acid, salicylic acid, and combinations thereof.

7. The medical implant according to claim 3, wherein the second reactant comprises a polymer having acid functional groups thereon, the acid functional groups selected from the group consisting of carboxylic acids, sulfonic acids, and combinations thereof.

8. The medical implant according to claim 1, wherein the first reactant comprises hydrolytically degradable bonds and the second reactant comprises a base.

9. The medical implant according to claim 8, wherein the base adjusts the pH of bodily fluid adjacent the medical implant to a pH from about 7.5 to about 9.5.

10. The medical implant according to claim 1, wherein the first reactant comprises enzymatically degradable linkages and the second reactant comprises an enzyme.

11. The medical implant according to claim 10, wherein the enzymatically degradable linkages comprise peptidic linkages, and the enzyme is selected form the group consisting of proteases, metalloproteinases, collagenases, and combinations thereof.

12. The medical implant according to claim 10, wherein the enzymatically degradable linkages are selected from the group consisting of amino acid residues, 2-mer to 6-mer oligopeptides, D-glucose, N-acetylgalactosamine, N-acetylneuraminic acid, N-acetylglucosamine, N-acetylmannnosamine, oligodeoxyadenine, oligodeoxyguanine, oligodeoxycytosine, oligodeoxythymidine; oligoadenine, oligoguanine, oligocytosine, oligouridine, and combinations thereof.

13. The medical implant according to claim 1, wherein the bioactive agent is selected from the group consisting of proteins, analgesics, growth factors, chemotherapeutics, and combinations thereof.

14. A medical implant comprising:
a mesh comprising a first reactant and at least one bioactive agent; and
a component for securing the mesh to tissue comprising a second reactant, the component selected from the group consisting of staples, sutures, clips, tacks, screws, pins, anchors, and fasteners,
wherein the second reactant degrades the first reactant, thereby releasing the bioactive agent in vivo.

15. The medical implant according to claim 14, wherein the first reactant comprises hydrolytically degradable bonds and the second reactant comprises an acid.

16. The medical implant according to claim 15, wherein the acid adjusts the pH of bodily fluid adjacent the medical implant to a pH from about 5 to about 7.5.

17. The medical implant according to claim 15, wherein the first reactant comprises a polymer possessing monomers selected from the group consisting of lactic acid, glycolic acid, lactide, glycolide, ε-caprolactone, trimethylene carbonate, dioxanones, azelaic acid, succinnic acid, adipic acid, sebacic acid, malonic acid, glutaric acid, ethyl dichlorophosphate, azelaic acid anhydride, sebacic acid anhydride, and combinations thereof.

18. The medical implant according to claim 15, wherein the second reactant is an acid selected from the group consisting of lactic acid, citric acid, acetic acid, stearic acid, salicylic acid, and combinations thereof.

19. The medical implant according to claim 15, wherein the second reactant comprises a polymer having acid functional groups thereon, the acid functional groups selected from the group consisting of carboxylic acids, sulfonic acids, and combinations thereof.

20. The medical implant according to claim 14, wherein the first reactant comprises hydrolytically degradable bonds and the second reactant comprises a base.

21. The medical implant according to claim 20, wherein the base adjusts the pH of bodily fluid adjacent the medical implant to a pH from about 7.5 to about 9.5.

22. The medical implant according to claim 14, wherein the first reactant comprises enzymatically degradable linkages and the second reactant comprises an enzyme.

23. The medical implant according to claim 22, wherein the enzymatically degradable linkages comprise peptidic linkages, and the enzyme is selected form the group consisting of proteases, metalloproteinases, collagenases, and combinations thereof.

24. The medical implant according to claim 22, wherein the enzymatically degradable linkages are selected from the group consisting of amino acid residues, 2-mer to 6-mer oligopeptides, D-glucose, N-acetylgalactosamine, N-acetylneuraminic acid, N-acetylglucosamine, N-acetylmannnosamine, oligodeoxyadenine, oligodeoxyguanine, oligodeoxycytosine, oligodeoxythymidine; oligoadenine, oligoguanine, oligocytosine, oligouridine, and combinations thereof.

25. The medical implant according to claim 14, wherein the bioactive agent is selected from the group consisting of proteins, analgesics, growth factors, chemotherapeutics, and combinations thereof.

\* \* \* \* \*